United States Patent
Cabeza Guillen et al.

(10) Patent No.: US 9,259,145 B2
(45) Date of Patent: Feb. 16, 2016

(54) APPARATUS AND METHOD FOR TESTING NIGHT VISION

(75) Inventors: Jesús Miguel Cabeza Guillen, Aalen (DE); Timo Kratzer, Aalen (DE)

(73) Assignee: CARL ZEISS VISION GMBH, Aalen (DE)

( * ) Notice: Subject to any disclaimer, the term of this patent is extended or adjusted under 35 U.S.C. 154(b) by 548 days.

(21) Appl. No.: 12/015,566

(22) Filed: Jan. 17, 2008

(65) Prior Publication Data

US 2008/0170206 A1    Jul. 17, 2008

Related U.S. Application Data

(63) Continuation of application No. PCT/EP2006/007031, filed on Jul. 18, 2006.

(30) Foreign Application Priority Data

Jul. 19, 2005  (DE) .......................... 10 2005 034 619

(51) Int. Cl.
*A61B 3/00* (2006.01)
*A61B 3/036* (2006.01)
(Continued)

(52) U.S. Cl.
CPC ................. *A61B 3/036* (2013.01); *A61B 3/032* (2013.01); *A61B 3/063* (2013.01)

(58) Field of Classification Search
USPC ......... 351/243, 246, 200, 205, 221, 206, 245, 351/203, 222; 356/614, 615, 620
See application file for complete search history.

(56) References Cited

U.S. PATENT DOCUMENTS 5,080,478 A * 1/1992 O'Brien et al. ............... 351/224
5,471,262 A * 11/1995 Trokel ............................ 351/239
5,550,602 A * 8/1996 Braeuning .................... 351/243
(Continued)

FOREIGN PATENT DOCUMENTS

DE   1 927 704    11/1965
DE   2 321 570    11/1974
(Continued)

OTHER PUBLICATIONS

European Examination Report for Application No. 06 762 667.1; Aug. 2013; 4 pp.
(Continued)

*Primary Examiner* — Stephone B Allen
*Assistant Examiner* — Brandi Thomas
(74) *Attorney, Agent, or Firm* — Harness, Dickey & Pierce, P.L.C.

(57) ABSTRACT

A method and an apparatus for testing night vision are disclosed. At least one visual mark is presented to a test person having an open pupil from a distance of several meters. The visual mark is configured as a light point, and a visual impression of the test person is determined by means of the visual mark. The apparatus comprises means for opening a pupil of a test person, in particular a darkened room. An examination position for the test person and a presentation apparatus for visual marks arranged at a distance of several meters from the examination position are also provided. The presentation apparatus comprises at least one point-shaped light source. A light beam thereof is directed towards the examination position. Means are provided for determining a visual impression of the test person with the help of the visual marks.

31 Claims, 2 Drawing Sheets

(51) Int. Cl.
*A61B 3/032* (2006.01)
*A61B 3/06* (2006.01)

(56) References Cited

U.S. PATENT DOCUMENTS

| | | | |
|---|---|---|---|
| 5,567,937 A * | 10/1996 | Pinkus | 250/252.1 |
| 5,870,168 A | 2/1999 | Kirchhuebel et al. | |
| 5,988,814 A | 11/1999 | Rohlfing et al. | |
| 6,196,845 B1 * | 3/2001 | Streid | 434/44 |
| 6,406,147 B1 * | 6/2002 | Hayashi et al. | 351/239 |
| 6,992,275 B1 * | 1/2006 | Knapp | 250/214 VT |
| 2001/0038425 A1 * | 11/2001 | Lee | 349/61 |
| 2002/0044259 A1 | 4/2002 | Oretega et al. | |
| 2005/0219693 A1 * | 10/2005 | Hartkop et al. | 359/462 |
| 2005/0225720 A1 * | 10/2005 | Ridings | 351/200 |
| 2006/0132472 A1 * | 6/2006 | Peeters et al. | 345/204 |

FOREIGN PATENT DOCUMENTS

| | | |
|---|---|---|
| DE | 30 03 588 C2 | 4/1985 |
| DE | 43 26 760 A1 | 3/1995 |
| DE | 197 29 102 C2 | 4/2002 |
| DE | 203 10 162 U1 | 11/2003 |
| EP | 0 830 838 A2 | 3/1998 |
| GB | 982874 | 2/1965 |
| GB | 2 355 540 A | 4/2001 |
| JP | 5-285107 | 11/1993 |
| JP | 2001-87225 | 4/2001 |
| JP | 2003-93344 | 4/2003 |
| WO | WO 02/078529 A1 | 10/2002 |

OTHER PUBLICATIONS

English translation of European Examination Report for Appl'n No. 06 762 667.1 dated Jan. 21, 2015; 4 pp.

* cited by examiner

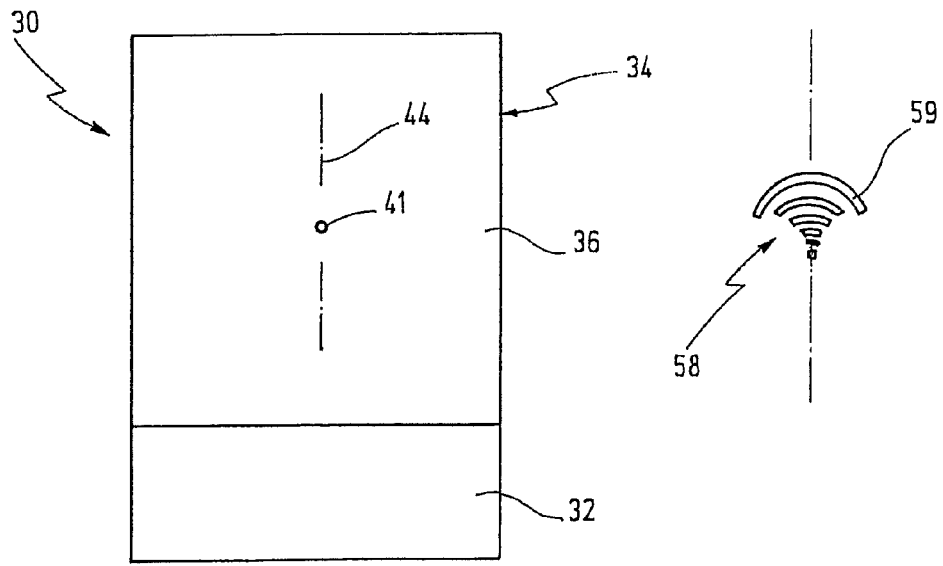
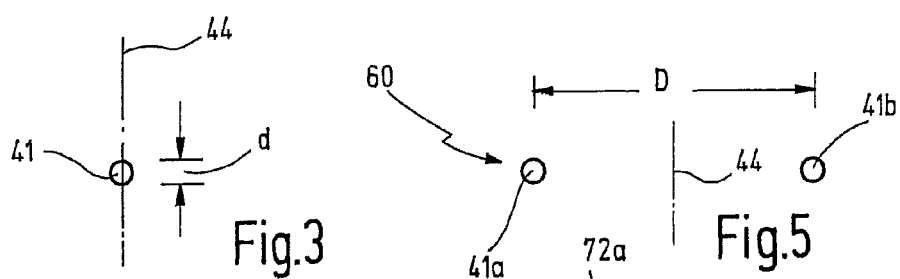
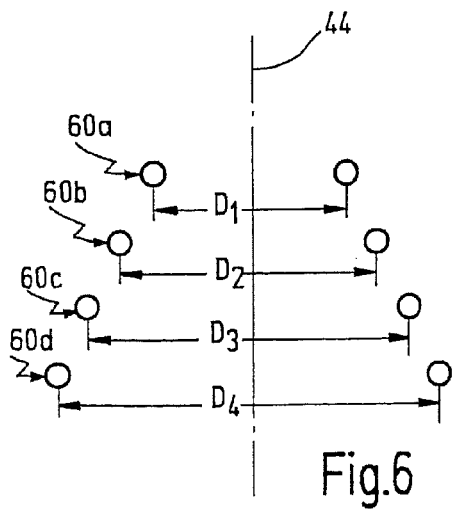
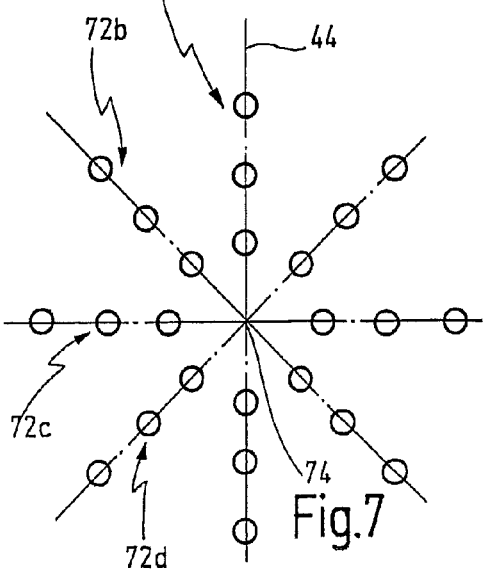
Fig.2　Fig.4　Fig.3　Fig.5　Fig.6　Fig.7

APPARATUS AND METHOD FOR TESTING NIGHT VISION

RELATED APPLICATIONS

This is a continuation application of copending International Application PCT/EP2006/007031 filed on Jul. 18, 2006 which has been published in German language and claims priority of German patent application 10 2005 034 619.7, filed Jul. 19, 2005, the contents of which is fully incorporated by reference herewith.

FIELD OF THE INVENTION

The invention is related to the field of night vision testing.

More specifically, the invention is related to a method for testing night vision in which, preferably in a darkened room, at least one visual mark is presented to a test person having an open pupil from a distance of several meters.

Moreover, the invention is related to an apparatus for testing night vision, comprising means for opening a pupil of a test person, preferably within a darkened room, an examination position for the test person, and a presentation apparatus for visual marks arranged at a distance of several meters from the examination position.

BACKGROUND OF THE INVENTION

The refractive properties of an eye depend, inter alia, from the pupil diameter. This means that a refraction measurement that was carried out under normal light conditions is longer valid for poor light conditions because the size of the pupil has increased. If, therefore, a person owns a spectacle that was optimized for daylight, the visual acuity at twilight, and, in particular during night driving in a vehicle, may be reduced because the spectacle is not optimized for these light conditions. As a consequence, it may happen that persons see very well at daytime, be it with or without a spectacle, whereas they are almost blind at night because the daytime refraction of their eyes is entirely different from their nighttime refraction.

In the prior art several methods and apparatuses have already been suggested for testing the visual behavior during twilight and in the darkness. Other phenomena are related thereto, like adaptation, i.e. the ability of the eye to adapt itself more or less quickly from bright ambient conditions to dark conditions.

For measuring the visual impression, in particular the visual acuity of an eye, subjective as well as objective approaches are known. The visual impression comprises the entire perception of the test person, i.e. including potential peripheral limitations in the field of his/her vision (tunnel vision) and limited areas of vision loss within the field of vision (skotoma). The visual acuity is related solely to the sharp vision, i.e. the recognition of details, independent from the above limitations.

With the subjective approach certain visual marks are presented to the test person for him/her to look at through a test spectacle into which test spectacle lenses are inserted one after the other by an examination person. The test person then informs the examination person with which test spectacle lens he/she can best see the visual mark, in particular in the sharpest way. Accordingly, the subjective ruling of the test person influences the examination.

With the objective approach, in contrast, one, for example, measures the refraction of the eye without any interaction with the test person, for example with a wavefront analyzer. This method, accordingly, results in an objectively optimum result which, however, in practice is not always congruent with the subjective impression of the test person. Therefore, both methods are often combined in order to achieve an optimum result.

In the field of apparatuses for measuring the vision of an eye, one distinguishes between those, in which the test person sits freely in a room and looks at visual marks appearing at a distance of several meters, further those configured as box-type tabletop devices into which the test person looks through two eyepieces, and finally those which the test person carries as goggles or helmets. The two last-mentioned apparatuses have the disadvantage that they may result in a so-called device-myopia because the test person does not look under normal conditions.

From German patent specification 30 03 588 C2 it is known to test twilight vision, flare stability and adaptation ability by means of an apparatus in which certain visual marks of predetermined brightness are projected onto a screen at predetermined ambient brightness. The test person is located at a distance of at least three meters from the screen. The visual marks are of known character, and are, for example, configured as Landolt rings. With such an apparatus a precise examination and determination of night visual acuity is impossible.

From U.S. Pat. No. 3,328,113 a device for testing night vision is known. With this prior art device peripheral light points are presented to the test person as visual marks. The light points are generated by means of a flickering light source and a rotatable aperture disk arranged in front thereof in connection with radial slits in the front plate of the device. The aperture disk is provided with openings of different diameter in the range of between 0.6 and 14 mm having different distances from the aperture disk axis of rotation. In this way one can present light points of different size and different distance from the axis of rotation by rotating the aperture plate arranged immediately behind the radial slits. A chin rest for the test person is arranged at about 40 cm in front of the device. With this prior art device one can, therefore, also just test the vision at darkness. A visual acuity measurement is not provided.

Besides the above, the prior art also describes tabletop devices (German disclosure document DE 23 21 570; U.S. Pat. No. 5,870,168; Japanese disclosure document JP 2001-087225 A) as well as helmet- or goggle-type apparatuses (German disclosure document DE 43 26 760 A1; German patent specification DE 197 29 102 C2) used, inter alia, for testing twilight vision, however use conventional visual marks, and, some of them flaring means for testing adaptation capability.

SUMMARY OF THE INVENTION

It is, therefore, an object underlying the invention to improve a method and an apparatus of the type specified at the outset such that the above-mentioned disadvantages are avoided. In particular, it shall become possible to examine the night visual acuity much more precisely than was hitherto possible. This makes it possible to provide concerned people with viewing aids with which they can see substantially sharper under twilight and night conditions. For vehicle drivers this means a significant gain in safety under the aforementioned ambient conditions.

In a method of the type specified at the outset this object is achieved in that the visual mark is configured as a light point and that the visual acuity of the test person is determined by means of the visual mark.

In an apparatus of the type specified at the outset this object is achieved in that the presentation apparatus comprises at least one point-shaped light source a light beam of which being directed towards the examination position, and that means are provided for testing the visual acuity of the test person with the help of the visual marks.

The object underlying the invention is, thus, entirely solved.

The invention namely frees itself from the prior art approach working with two-dimensional visual marks. With these marks there is always a certain background illumination present which makes an exact determination of an optimum visual acuity correction impossible, when a test spectacle is put on the test person and different test spectacle lenses are inserted one after another.

In contrast, according to the invention a light source configured as a point as well as possible is used as a visual mark. The test person sees this light point with an enlarged circular or elliptical contour, depending on his/her defective vision and, above all, with laterally falling flanges. These flanges have their origin in the so-called point spread function (PSF). The PSF causes for an ideal, i.e. aberration-free system focused to infinity that the light distribution in the image of a point-shaped light source being infinitely away has an intensity function in the shape of a first order Bessel function with a narrow tip and laterally falling flanges in a radial direction away from the center. These flanges can be perceived by the test person only at almost absolute darkness. As soon as there is a relatively weak ambient brightness the flanges disappear therein and are no more perceivable.

The measurement in a dark room has the advantage that the test person's pupil is wide open which, for example corresponds to a much higher degree to the conditions of a night drive as the circumstances of a conventional measurement, in which due to the presence of residual light the pupils are not entirely open. According to the method of the invention, due to the point-shaped light source only a significantly lower light intensity enters into the eye, compared with conventional visual mark tables with illuminated background. This does, of course, not exclude that also a flare can be simulated in the context of the present invention.

If, therefore, one proceeds according to the present invention, one can offer to a test person different test spectacle lenses one after the other and the test person is well in a position to indicate exactly with which test spectacle lens his vision is sharpest, namely when the tip as viewed by him/her is narrowest and the laterally falling flanges are at a minimum.

Opthalmological examination procedures and apparatuses utilizing point-shaped light sources are known in the prior art.

U.S. Pat. No. 6,540,356 B1, for example, describes a so-called Tscherning aberrometer. With this prior art apparatus an objective measurement in the meaning of the above definition is made, i.e. without interaction by the test person. One or more narrow, collimated beams are generated by means of light emitting diodes and are projected onto the eye of the test person. The deflection of the beams onto the plane of the retina is measured. In contrast, the present invention utilizes a point-shaped light source capturing the eye as spherical waves. No deflection is measured.

In other known apparatuses (JP 05-285107 A; JP 2003-093244 A; U.S. Pat. No. 5,080,478; DE 197 29 102 C2) light emitting diodes are utilized as point-shaped light sources, however, the generated light points are used as fixation targets or as stimuli, for testing adaptation capability.

In a preferred embodiment of the invention, the light point or the light beam emitted by the light source has a diameter of less than 1 mm.

This dimensioning has turned out in practice to be an optimum compromise between, on the one hand, a diameter as small as possible, i.e. a light source being as point-shaped as possible, and, on the other hand a maximum in brightness requiring a certain diameter. Preferably, a diameter of about 0.9 mm is used which, for a distance of about 6 m, is appropriate for a patient with visual acuity 2 (40/20).

In a preferred improvement of the inventive method, the visual mark consists of at least one pair of light points, or, for the inventive apparatus, at least one pair of light sources is provided, each arranged at a predetermined distance from one another.

This measure has the advantage that one can additionally check whether the test person can see only one light point or two under such circumstances.

In a further refinement of this embodiment, the visual mark may consist of several pairs of light points or light sources, wherein, preferably, the pairs are arranged parallel to one another and have a different distance from one another.

This measure has the advantage that a still more precise visual acuity determination is possible, similar as if a Landolt ring were used as a visual mark.

In a further embodiment, the visual mark consists of several rows of light points, wherein, preferably, the rows are straight and intersect at a common section point.

This measure has the advantage that in addition an astigmatism of the test person may be detected.

According to the invention, the point-shaped light source may be put into practice in various ways.

In a first alternate embodiment, the at least one point-shaped light source is configured as an aperture with an opening and lamp means arranged behind the opening.

This measure has the advantage that a very simple design results and that lamp means of different kinds may be used.

In a second alternate embodiment, the at least one point-shaped light source is configured as a light-emitting diode.

This measure has the advantage that well-established and proven components may be used having a low energy consumption and the intensity of which may be set in a simple manner.

In a third alternate embodiment, the at least one point-shaped light source is configured by a light point of a screen.

This measure has the advantage that a planar structure is provided for generating a light point, such that, on the one hand, the light point position within the plane may be freely predetermined, and, on the other hand, certain patterns of light points may be generated, for example the pairs and rows already mentioned above, in particular in different shape and time sequence.

Insofar it is preferred when the screen is a LED screen, in particular an OLED screen.

This measure has the advantage that large areas with a high intensity of the light points may be realized.

As an alternative, the screen may be a backlight screen with an aperture plate in front thereof, in particular a liquid crystal aperture plate.

Finally, there is one more embodiment of the inventive apparatus, in which a magazine of test spectacle lenses for a test spectacle worn by the test person is associated to the examination position.

This measure has the advantage that an examination person can offer to a test person different test spectacle lenses, as known per se, in order to determine those lenses which are optimal for the test person.

Further advantages will become apparent from the description and the enclosed drawing.

It goes without saying that the features mentioned before and those that will be explained hereinafter may not only be used in the particularly given combination but also in other combinations or alone without leaving the scope of the present invention.

Embodiments of the invention are depicted in the drawings and will be explained in further detail in the subsequent description.

It will be understood that the features of the invention mentioned above and those yet to be explained below can be used not only in the respective combination indicated, but also in other combinations or in isolation, without leaving the scope of the present invention.

BRIEF DESCRIPTION OF THE DRAWINGS

Exemplary embodiments of the invention are explained in more detail in the following description and are represented in the drawings, in which:

FIG. 2 shows a front elevational view of a presentation apparatus used in the apparatus of FIG. 1;

FIG. 3 shows a first embodiment of a visual mark used for the present invention and having the shape of a light point;

FIG. 4 shows the point-shaped visual mark of FIG. 3, as perceived by a test person with defective vision;

FIG. 5 shows a second embodiment of a visual mark used for the present invention and having the shape of a pair of light points;

FIG. 6 shows a third embodiment of a visual mark used for the present invention and having the shape of several pairs of light points; and FIG. 7 shows a fourth embodiment of a visual mark used for the present invention and having the shape of several rows of light points.

DETAILED DESCRIPTION OF THE PREFERRED EMBODIMENTS

Figure 1:
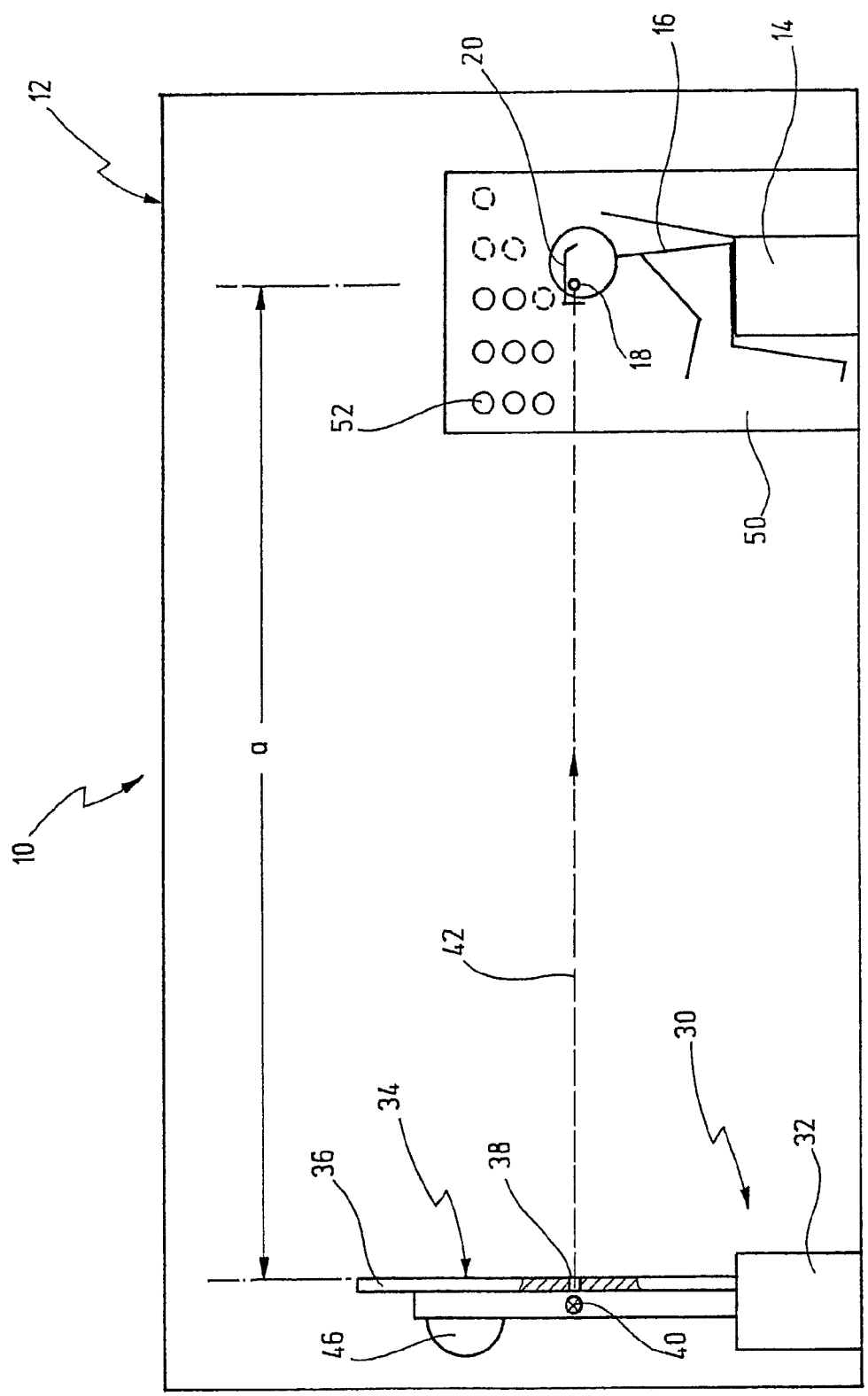
FIG. 1 shows a highly schematic side elevational view of an embodiment of an inventive apparatus.

In FIG. 1, reference numeral 10 designates as a whole an embodiment of an apparatus for checking night visual acuity according to the present invention with which the method according to the present invention may be executed.

For the present invention it is important that the pupils of the test person be open. For that purpose, apparatus 10 comprises a preferably darkened room 12. The term "darkened" is to be understood to mean that the room is light-tight to the exterior and is totally dark after an ambient or point-shaped orientation illumination has been switched off. This does, of course, not exclude that a certain brightness may be set within room 12 and that the pupils are opened artificially by administering an appropriate agent (atropine drops). The preferred operational mode, however, is the total darkness because the test person then has fully open pupils after a certain adaptation time.

At the right hand end of FIG. 1, there is provided within room 12 an examination position 14 for a test person 16, in the simplest embodiment a chair. In FIG. 1 an eye of test person 16 is shown at 18. Test person 16 wears a test spectacle 20 of conventional design into which an examination person may insert different test spectacle lenses.

At the left hand end of FIG. 1 there is provided within room 12 a presentation apparatus 30 for visual marks. Presentation apparatus 30 is located at a distance "a" from examination position 14. Distance "a" shall be as long as possible and, in practice, shall be of the order of several meters, for example 6 meters.

Presentation apparatus 30 is provided with a base 32 supporting a visual mark source 34. Visual mark source 34 may be configured in various ways.

In the embodiment shown in FIG. 1, visual mark source 34 consists of an aperture 36 having a central opening 38. A lamp means 40 is located behind opening 38. In this way, a point-shaped light source 41 or a light point is generated as a visual mark, as is shown in the front elevational view of FIG. 2. Point-shaped light source 41 emits a light beam 42 directed towards examination position 14 and falling into eye 18 of test person 16.

FIGS. 2 and 3 show that point-shaped light source 41 or light point is located on an axis 44. Light point 41 has a diameter "d" being smaller than 1 mm. A diameter of 0.9 mm is preferred. This value is appropriate at a distance "a" of about 6 m for a test person 16 having a visual acuity of 2 (40/20). Other visual marks may also be generated relative to axis 44, as will be explained further below with reference to FIGS. 5 to 7.

Within room 12, there is, further, provided an indirect illumination 46. Indirect illumination 46 may be located on the rear side of presentation apparatus 30, and may be adapted to be set that a certain brightness is generated within room 12 for measuring or orientation purposes. Illumination 46 may also be configured and located such that it is appropriate for flaring test person 16 for a short period of time for simulating flare situations as may occur during night driving.

Moreover, there is also provided within room 12 a magazine 50 for test spectacle lenses in the vicinity of examination position 14 for enabling an examination person to insert test spectacle lenses 52 one after another into test spectacle 20 worn by test person 16, as already explained. An orientation illumination may also be provided there (not shown).

FIG. 4 shows a visual mark 58 as perceived by a test person 16 having defective vision. Perceived visual mark 58 has a circular or elliptic contour with a transition into laterally falling flanges 59. This shape of perceived visual mark 58 is caused by the so-called point spread function (PSF) already discussed at the outset.

As already mentioned, the PSF causes for an ideal, i.e. aberration-free system focused to infinity that the light distribution in the image of a point-shaped (diameter d) light source 41 being at a distance "a" has an intensity function in the shape of a first order Bessel function with a narrow tip and laterally falling flanges in a radial direction away from the center. In the case of a myopia or a hyperopia of test person 16 the PSF's reaction is quite sensitive and obtains the shape of a circle instead a narrow tip, the diameter of the circle being an indication for the defective vision; in the case of an astigmatism the shape becomes elliptic.

In any event the laterally falling flanges remain and their magnitude as perceived by test person 16 is an indication to which extent the defective vision was already corrected by inserting respective test spectacle lenses 52 into test spectacle 20, namely with wide open pupils within the surrounding darkness. With increasing correction perceived visual mark 58 in FIG. 4, therefore, becomes narrower until, ideally, it assumes the shape of a narrow tip with minimum lateral flanges 59. This constitutes a major advantage of the invention because the measurement within a dark room 12 has the effect that test person 16 can very well recognize laterally falling flanges 59 which is already no longer possible at low ambient light.

FIG. 5 shows an alternate embodiment in which several pairs 60a, 60b, 60c, and 60d are arranged parallel to one another along axis 44, wherein pairs 60a, 60b, 60c, and 60d have increasing distances $D_1$, $D_2$, $D_3$, and $D_4$. Such patterns allow to determine the visual acuity particularly well, similar to prior art visual marks having the shape of Landolt rings.

Finally, FIG. 7 shows another alternate embodiment with four rows 72a, 72b, 72c, and 72d of six light points, rows 72a, 72b, 72c, and 72d being normally oriented differently and, in the embodiment shown, intersect at an intersection point 74 under equal angles of 45°. This arrangement allows to additionally examine the astigmatism of test person 16.

As already mentioned above, various practical designs come into consideration for point-shaped light source 41. Besides the backlighted aperture arrangement of FIG. 1 one can, preferably, also work with light emitting diodes (LED). Light emitting diodes are nowadays available in very small dimensions (diameter down to 0.200 µm including socket). Its brightness may easily be set by adjusting the supply current. They need only a small supply voltage of typically 5 V and have a high efficiency.

In particular for the generation of patterns of light points (FIGS. 5 to 7), planar displays of high brightness are appropriate. These displays may be LED displays, in particular OLED displays utilizing organic light emitting diodes and having a particularly large area. As an alternative one can also use a backlighted planar display being provided with a controllable aperture device, for example a liquid crystal device (LCD) which allows to optically switch on or off individual pixels by selective shadowing.

The invention claimed is:

1. A method for testing night vision comprising:
presenting at least one visual mark to a test person in a darkened room so that the test person has an open pupil for testing;
presenting the visual mark to the test person from an actual distance of several meters;
configuring the visual mark as an isolated light point produced by a LED or OLED light source, wherein the visual mark is the only light presented to the test person; and
determining an optimum visual acuity correction of said test person by means of said visual mark.

2. The method of claim 1, wherein said light point has a diameter of less than 1 mm.

3. The method of claim 2, wherein said visual mark consists of at least one pair of isolated light points arranged at a predetermined distance from one another.

4. The method of claim 3, wherein said visual mark consists of several pairs of isolated light points.

5. The method of claim 4, wherein said pairs are arranged parallel to one another and have a different distance from one another.

6. The method of claim 1, wherein said visual mark consists of several rows of isolated light points.

7. The method of claim 6, wherein said rows are straight and intersect at a common section point.

8. An apparatus for testing night vision, comprising a darkened room for opening a pupil of a test person, an examination position for said test person, a presentation apparatus for visual marks arranged at an actual distance of several meters from said examination position, wherein said visual marks are the only light presented to the test person and comprise exclusively one or more isolated point-shaped LED or OLED light sources, a light beam of which being directed towards said examination position, and means for determining an optimum visual acuity correction of said test person with the help of said visual marks.

9. The apparatus of claim 8, wherein said light beam emitted by said light source has a diameter of less than 1 mm.

10. The apparatus of claim 8, wherein at least one pair of isolated light point sources is provided, said light sources being arranged at a predetermined distance from one another.

11. The apparatus of claim 10, wherein several pairs of isolated light point sources are provided.

12. The apparatus of claim 11, wherein said pairs are arranged parallel to one another and have a different distance from one another.

13. The apparatus of claim 8, wherein several rows of isolated light point sources are provided.

14. The apparatus of claim 13, wherein said rows are straight and intersect at a common section point.

15. The apparatus of claim 8, wherein said at least one isolated point-shaped light source is configured by a light point of a screen.

16. The apparatus of claim 15, wherein said screen is a backlight screen with an aperture plate in front thereof.

17. The apparatus of claim 16, wherein said aperture plate is a liquid crystal aperture plate.

18. The apparatus of claim 8, wherein said means for determining an optimum visual acuity correction includes a magazine of different test spectacle lenses for a test spectacle worn by said test person which is provided at said examination position for selective placement in said test spectacle.

19. A method for testing night vision comprising:
presenting at least one visual mark to a test person in a darkened room so that the test person has an open pupil for testing;
presenting the at least one visual mark to the test person from an actual distance of several meters;
configuring the at least one visual mark as an isolated light point having a diameter of less than 1 millimeter, and
determining an optimum visual acuity correction of said test person by means of said visual mark.

20. The method of claim 19 wherein the isolated light point is the only visual mark and the only light presented to the test person.

21. The method of claim 19, wherein the diameter of the light point is 0.9 millimeters and the distance from the visual mark to the test person is 6 meters.

22. A method for testing night vision comprising:
presenting at least one visual mark to a test person from an actual distance of several meters within a completely dark enclosure so that a pupil of the test person is fully open for testing;
presenting the visual mark as the only light to the test person,
configuring the visual mark as an isolated light point; and
determining an optimum visual acuity correction of the test person by means of said visual mark.

23. The method of claim 22, wherein said visual mark is produced by a LED or OLED light source.

24. The method of claim 22, wherein the light point has a diameter of less than 1 millimeter.

25. The method of claim 22, wherein a single light point is the only visual mark.

26. The method of claim 22, wherein the diameter of the light point is 0.9 millimeters and the distance from the visual mark to the test person is 6 meters.

27. An apparatus for testing night vision, comprising a darkened room for opening a pupil of a test person, an examination position for said test person, a presentation apparatus for visual marks arranged at an actual distance of several meters from said examination position, wherein said presentation apparatus comprises at least one isolated point-shaped light source having a diameter of less than 1 millimeter, a light beam of which being directed towards said examination position, and means for determining an optimum visual acuity correction of said test person in accordance with how the test person sees the light point.

28. An apparatus for testing night vision, comprising:
- a completely dark enclosure for fully opening a pupil of a test person located in an examination position in said enclosure,
- a presentation apparatus for one or more visual marks arranged at an actual distance of several meters from said examination position, wherein each of said one or more visual marks is configured as an isolated point-shaped light source with a light beam therefrom being directed towards said examination position, wherein the light from said one or more visual marks is the only light presented to the test person, and
- means for determining an optimum visual acuity correction of said test person in accordance with how the test person sees the light point.

29. The apparatus of claim 28, wherein a single isolated light point is the only visual mark.

30. An apparatus for testing night vision, comprising:
- a completely dark enclosure for fully opening a pupil of a test person located in an examination position in said enclosure,
- a presentation apparatus for visual marks arranged at an actual distance of several meters from said examination position, wherein said presentation apparatus comprises at least one isolated point-shaped light source, a light beam of which being directed towards said examination position, such that the light from said point-shaped light source is the only light presented to the test person so that a test person with defective night vision sees a distorted image of the light point with enlarged circular or elliptical contours with laterally falling flanges, and
- means for determining an optimum visual acuity correction of said test person that minimizes the distortion of said image.

31. The apparatus of claim 30, wherein the light point has a diameter of less than 1 mm.

* * * * *